United States Patent [19]
Callan et al.

[11] Patent Number: 5,935,906
[45] Date of Patent: Aug. 10, 1999

[54] AMINOETHOXYVINYLGLYCINE IN COMBINATION WITH MEPIQUAT CHLORIDE

[75] Inventors: Mary Callan, Limburgerhof, Germany; Warren E. Shafer, Libertyville, Ill.; Candace L. Black-Schafer, Libertyville, N.C.

[73] Assignee: BASF Corporation, Mt. Olive, N.J.

[21] Appl. No.: 08/777,716

[22] Filed: Dec. 20, 1996

Related U.S. Application Data

[60] Provisional application No. 60/009,298, Dec. 21, 1995.

[51] Int. Cl.$^6$ .............................. A01N 37/06; A01N 43/40
[52] U.S. Cl. ........................ 504/130; 504/147; 504/174; 504/177; 504/182; 504/248; 504/320
[58] Field of Search ...................... 504/130, 147, 504/248, 320, 182, 174, 177

[56] References Cited

U.S. PATENT DOCUMENTS

| | | | |
|---|---|---|---|
| 3,787,198 | 1/1974 | Hagimoto et al. | 504/134 |
| 3,876,782 | 4/1975 | Kishino et al. | 514/113 |
| 3,894,123 | 7/1975 | Kishino et al. | 558/174 |
| 3,928,586 | 12/1975 | Sledzinski et al. | 514/136 |
| 3,970,728 | 7/1976 | Kishino et al. | 558/185 |
| 4,002,458 | 1/1977 | Hofacker | 71/27 |
| 4,124,227 | 11/1978 | Ruis | 503/224 |
| 4,181,715 | 1/1980 | Kondo et al. | 424/127 |
| 4,217,130 | 8/1980 | Tsurata et al. | 504/287 |
| 4,220,464 | 9/1980 | Martin | 504/312 |
| 4,227,918 | 10/1980 | Hofer et al. | 504/350 |
| 4,277,364 | 7/1981 | Shasha et al. | 56/10.8 |
| 4,344,857 | 8/1982 | Shasha et al. | 504/244 |
| 4,347,372 | 8/1982 | Fory et al. | 548/217 |
| 4,382,813 | 5/1983 | Shasha | 504/220 |
| 4,388,464 | 6/1983 | Kristinsson et al. | 548/136 |
| 4,486,218 | 12/1984 | Reiser et a. | 548/262 |
| 4,531,964 | 7/1985 | Shimano et al. | 548/302 |
| 4,534,783 | 8/1985 | Beestman | 71/27 |
| 4,561,880 | 12/1985 | Shimano et al. | 548/264 |
| 4,563,212 | 1/1986 | Becher et al. | 71/DIG. 1 |
| 4,594,099 | 6/1986 | Yamada et al. | 548/513 |
| 4,608,076 | 8/1986 | Gladon et al. | 504/182 |
| 4,640,709 | 2/1987 | Beestman | 71/DIG. 1 |
| 4,647,302 | 3/1987 | Reiser et al. | 514/383 |
| 4,659,722 | 4/1987 | Nakagawa et al. | 514/332 |
| 4,690,934 | 9/1987 | Yoshida et al. | 514/354 |
| 4,715,883 | 12/1987 | Lukaszczyk et al. | 504/106 |
| 4,729,783 | 3/1988 | Regel et al. | 514/383 |
| 4,743,293 | 5/1988 | Reiser et al. | 548/262 |
| 4,744,811 | 5/1988 | Schulz et al. | 504/319 |
| 4,749,405 | 6/1988 | Reiser et al. | 514/184 |
| 4,785,048 | 11/1988 | Chao | 427/146 |
| 4,804,762 | 2/1989 | Yoshida et al. | 514/336 |
| 4,851,035 | 7/1989 | Pirrung et al. | 504/320 |
| 4,871,766 | 10/1989 | Tsuda et al. | 514/521 |
| 4,911,952 | 3/1990 | Doane et al. | 71/DIG. 1 |
| 4,923,503 | 5/1990 | Schulz et al. | 504/274 |
| 4,936,901 | 6/1990 | Surgant et al. | 501/133 |
| 4,956,129 | 9/1990 | Scher et al. | 264/4.7 |
| 4,997,642 | 3/1991 | Curtis et al. | 424/681 |
| 5,024,937 | 6/1991 | Penticoff et al. | 435/41 |
| 5,037,716 | 8/1991 | Moffat | 430/109 |
| 5,069,711 | 12/1991 | Fischer et al. | 504/246 |
| 5,078,888 | 1/1992 | Penticoff et al. | 210/639 |
| 5,087,456 | 2/1992 | Meinard et al. | 424/501 |
| 5,089,046 | 2/1992 | Lee et al. | 504/207 |
| 5,125,959 | 6/1992 | Suyama et al. | 504/253 |
| 5,126,360 | 6/1992 | Dutzmann et al. | 514/383 |
| 5,130,131 | 7/1992 | Narayanan et al. | 424/94.65 |
| 5,135,942 | 8/1992 | Dutzmann et al. | 514/383 |
| 5,139,774 | 8/1992 | Meinard et al. | 71/DIG. 1 |
| 5,160,529 | 11/1992 | Scher et al. | 71/DIG. 1 |
| 5,221,318 | 6/1993 | Fischer et al. | 504/283 |
| 5,223,526 | 6/1993 | McLoughlin et al. | 514/406 |
| 5,228,896 | 7/1993 | Misslitz et al. | 504/288 |
| 5,250,505 | 10/1993 | Kast et al. | 504/292 |
| 5,310,721 | 5/1994 | Lo | 504/116 |
| 5,330,965 | 7/1994 | Misslitz et al. | 504/244 |
| 5,332,584 | 7/1994 | Scher et al. | 424/408 |
| 5,364,834 | 11/1994 | Kirchner et al. | 504/319 |
| 5,374,609 | 12/1994 | Kast et al. | 504/344 |
| 5,403,812 | 4/1995 | Kast et al. | 504/100 |
| 5,407,896 | 4/1995 | Kast et al. | 504/100 |
| 5,420,148 | 5/1995 | Dehne et al. | 514/395 |
| 5,433,173 | 7/1995 | Markles | 119/231 |
| 5,439,926 | 8/1995 | Dutzmann et al. | 514/383 |
| 5,446,067 | 8/1995 | Benoit et al. | 514/640 |
| 5,464,769 | 11/1995 | Attree et al. | 435/240.4 |
| 5,466,460 | 11/1995 | McMahon et al. | 424/408 |
| 5,705,648 | 1/1998 | Clark et al. | 546/349 |
| 5,801,119 | 9/1998 | Venburg et al. | 504/115 |

FOREIGN PATENT DOCUMENTS

| | | |
|---|---|---|
| 0 535 415 | 4/1993 | European Pat. Off. |
| 2 081 700 | 2/1982 | United Kingdom. |
| WO 93 07746 | 4/1993 | WIPO. |

OTHER PUBLICATIONS

Abeles; "Abscission: Role of Cellulase"; (1969) 44:447–452; *Plant Physiol.*

Amagasa, et al.; "The Mode of Flower–Inhibiting Action of Ethylene in Pharbitis nil"; (1987) 28(6):1159–1161; *Plant Cell Physiol.*

Atsmon, et al; "Comparative effects of gibberellin, silver nitrate and aminoethoxyvinyl glycine on sexual tendency and ethylene evolution in the cucumber plant"; (1979) 20(8):1547–1555; *Plant and Cell Physiol.*

BASF Corporation; "Pix® plant regulator—Results in Cotton (Southwest)"; (1987); *Technical Information Bulletin No. 8626.*

(List continued on next page.)

*Primary Examiner*—John Pak

[57] ABSTRACT

Provided are compositions and methods of improving a plant growth factor. The compositions and methods contain combinations of aminoethoxyvinylglycine and mepiquat chloride. The compositions provide an improvement in a plant growth factor, such as an increase in yield in cotton plant.

3 Claims, No Drawings

OTHER PUBLICATIONS

Beyer, et al; "Abscission: The Role of Ethylene Modification of Auxin Transport"; (1971) 48:208–212; *Plant Physiol.*

Cockshull, et al.; "2–Chloroethylphosphonic acid and flower initiation by *Chrysanthemum morifolium* Ramat, in short days and in long days"; (1978) 53:85–90; *Journal of Horticultural Science.*

Gianfagna, et al; "Mode of action and use of plant growth retardants in reducing the effects of environmental stress on horticultural crops"; (1992) 778–787; *Plant Growth Regulation.*

Grossmann, et al; "Inhibition of Ethylene Production in Sunflower Cell Suspensions by a Novel Oxime Ether Derivative"; (1991) 10:163–166; *Journal of Plant Growth Regulation.*

Guinn; "Abscission of Cotton Floral Buds and Bolls as Influenced by Factors Affecting Photosynthesis and Respiration"; (1974) 14:291–293; *Crop Science.*

Guinn; "Effects of Some Organic Solvents on Ethylene Evolution From Young Cotton Bolls"; (1977) 60:446–448; *Plant Physiol.*

Guinn; "Fruit Age and Changes in Abscisic Acid Content, Etylene Production, and Abscission Rate of Cotton Fruits"; (1982) 69:349–353; *Plant Physiol.*

Guinn; "Hormonal Relations in Flowering, Fruiting, and Cutout"; 265–272; *Western Cotton Research Laboratory.*

Guinn; "Nutritional Stress and Ethylene Evolution by Young Cotton Bolls"; (1976) 16:89–91; *Crop Science.*

Hoffmann; "Use of plant growth regulators in arable crops: Survey and outlook"; (1992) 798–808; *Progress in Plant Growth Regulation.*

Kirchner, et al; "Effects of novel oxime ether derivatives of aminooxyacetic acid on ethylene formation in leaves of oilseed rape and barley and on carnation flower senescence"; (1993) 13:41–46; *Plant Growth Regulation.*

Koning; "Control of Flower Opening by Plant Hormones in Gaillardia Grandiflora"; (1981) 40–67; *Dissertation, University of Michigan.*

Lay–Yee, et al.; "Changes in Cotyledon mRNA during Ethylene Inhibition of Floral Induction in Pharbitis nil Strain Violet"; (1987) 84:545–548; *Plant Physiol.*

Lipe, et al; "Ethylene, a Regulator of Young Fruit Abscission"; (1973) 51:949–953; *Plant Physiol.*

Lipe, et al; "Ethylene: Role in Fruit Abscission and Dehiscence Processes"; (1972) 50:759–764; *Plant Physiol.*

Machackova, et al; "Reversal of IAA–Induced Inhibition of Flowering by Aminoethoxyvinylglycine in Chenopodium"; (1986) 4:203–209; *Journal of Plant Growth Regulation.*

Owens, et al; "Induction of Perfect Flowers on Gynoecious Muskmelon by Silver Nitrate and Aminoethoxyvinylglycine"; (1980) 15(5):654–655; *Hort Science.*

Owens, et al; "Induction of Staminate Flowers on Gynoecious Cucumber by Aminoethoxyvinylglycine"; (1980) 15(3):256–257: *HortScience.*

Stanley, et at.; "The site of ethephon application and its effect on flower initiation and growth of chrysanthemum"; (1989) 64(3)341–350; *Journal of Horticultural Science.*

Suge; "Inhibition of photoperiodic floral induction in Pharbitis nil by ethylene"; (1972) 13:1031–1038; *Plant & Cell Physiol.* van Altvorst, et al; "The role of ethylene in the senescence of carnation flowers, a review"; (1995) 16:43–53; *Plant Growth Regulation.* van Doorn, et al; "Developments in the use of growth regulators for the maintenance of post–harvest quality in cut flowers and potted plants"; (1991) 298:195–208; *Acta Horticulturae.*

Veen; "Use of Inhibitors of Ethylene Action"; (1987) 201:213–222; *Acta Horticulturae.*

White, et al; "Environmental control of ethylene biosynthesis"; (1992) 147–155; *Progress in Plant Growth Regulation.*

Woltering, et al; "Amino–oxyacetic acid: analysis and toxicology"; (1987) 216:273–280; *Acta Horticulturae.*

F. Bangerth "The Effect of a Substituted Amino Acid on Ethylene Biosynthesis, Respiration, Ripening and Preharvest Drop of Apple Fruits" *Chemical Abstracts* vol. 89, No. 1 (Jan., 1979) Abstract No. 454608, (*J.Am.Soc.Hortic.Sci.* vol. 103, No. 3 (1978) pp. 401–404).

D.W. Greene. "Effect of Silver Nitrate, Aminoethoxyvinylglycine, and Gibberellins A4+7 plus 6–Benzylamino Purine on Fruit Set and Development of 'Delicious' Apples" *Chemical Abstracts,* vol 93, No. 21 (Nov., 1980) Abstract No. 199123 (*J.Am.Soc.Hortic.Sci.* vol. 105, No. 5 (1980) pp. 717–720).

Database WPI, Section CH, Week 9546, *Derwent Publications Ltd.,* Class C03, AN 95–351558 [AU 13625 95 A (Rhone Poulenc Agrcchimie) (Sep., 1995) US 5 478 796 A (Dec. 1995)].

International Search Report for PCT/US 96/20596 dated May 26, 1997.

Written Opinion International Application No. PCT/US96/20596, Filed Dec. 20, 1996.

AMINOETHOXYVINYLGLYCINE IN COMBINATION WITH MEPIQUAT CHLORIDE

This application claims the benefit of U.S. Provisional Application Number 60/009,298 filed on Dec. 21, 1995.

NOTICE OF COPENDING PATENT APPLICATIONS

The following patent applications are copending in the United States Patent and Trademark Office with this application:

1. Low Rate Application of Inhibitors of Ethylene Biosynthesis or Action, U.S. patent application Ser. No. 08/770,492, filed on Dec. 20, 1996, now U.S. Pat. No. 5,834,403, and incorporated herein by reference;

2. Encapsulated Plant Growth Regulator Formulations, U.S. patent application Ser. No. 08/771,319, filed on Dec. 20, 1996, now U.S. Pat. No. 5,837,653, and incorporated herein by reference;

3. Encapsulated Plant Growth Regulator Formulations And Applications, U.S. patent application Ser. No. 08/771,734, filed on Dec. 20, 1996 and incorporated herein by reference.

4. Encapsulated Plant Growth Regulator Formulations In Combination With Plant Growth Retardants, U.S. patent application Ser. No. 08/771,769, filed on Dec. 20, 1996 and incorporated herein by reference.

5. Plant Growth Regulators In Pyrrolidone Solvents, U.S. patent application Ser. No. 08/771,768, filed on Dec. 20, 1996, now abandoned, and incorporated herein by reference;

6. Enhancing The Rate of Seed Germination With Application of Ethylene Biosynthesis Inhibitors, U.S. patent application Ser. No. 08/770,789, filed on Dec. 20, 1996, now abandoned, and incorporated herein by reference; and 7. Plant Growth Retardants In Combination With Inhibitors Of Ethylene Biosynthesis Or Action, U.S. patent application Ser. No. 08/770,788, filed on Dec. 20, 1996 and incorporated herein by reference.

FIELD OF THE INVENTION

The present invention is related generally to the field of agriculture and specifically to compositions and use of plant growth regulators.

BACKGROUND OF THE INVENTION

Agriculture workers actively seek ways to improve the economic output of commercial crops. For example, in cotton crops, workers seek to improve such growth factors as increased boll set, increased floral initiation, decreased floral abscission increased germination, decreased boll abscission, and enhanced root growth. Workers also seek to increase plant tolerance to environmental stress.

Formulations containing plant growth regulators (PGRs) have been developed to improve the economic yield of agricultural plants. Plant growth retardants and inhibitors of ethylene biosynthesis or action are two types of PGRs. Some plant growth retardants have been shown to inhibit gibberellin biosynthesis resulting in the reduction of shoot height in small grains and cotton. This reduction in shoot height has a strong economic benefit since it provides for less lodging in small grains and reduction of excessive vegetative growth. It also provides more uniform ripening in cotton.

Three groups of gibberellin biosynthesis inhibitors are known. The first group encompasses compounds with quaternary ammonium, phosphonium or sulphonium moieties. One example of a compound from this group is mepiquat chloride, described in U.S. Pat. No. 3,905,798 and incorporated herein by reference. Mepiquat chloride may increase cotton yields, boll load, lint yield and seed yield. Mepiquat chloride is also known to reduce vegetative growth, plant height and boll rot. Mepiquat chloride also induces uniform ripeness if the plants are treated early during their development. Chloromequat chloride is also a representative compound of this group.

The second group of plant growth retardants encompasses compounds with a nitrogen containing heterocycle such as flurprimidol, paclobutrazol, uniconazole and ancymidol.

The third group encompasses acylcylcohexanediones (such as trinexapac-ethyl and prohexadione-Ca) and daminozide.

It is known that ethylene is involved in plant senescence and plant stress reactions. Ethylene is also involved in leaf, flower, and fruit abscission. Hence, agents that inhibit or regulate the production of ethylene in plants or control its action have been developed in an effort to improve the yield of agricultural crops. Inhibitors of ethylene biosynthesis include substituted oxime-ethers as described in U.S. Pat. No. 4,744,811, incorporated herein by reference. These compounds are also described in PCT Application WO 95-02211, incorporated herein by reference, as being soil amendment compositions that increase the assimilation of nitrogen by higher plants.

Other inhibitors of ethylene biosynthesis and action include aminoethoxyvinylglycine ("AVG"), aminooxyacetic acid ("AOA"), rhizobitoxine, and methoxyvinyl glycine ("MVG"). Silver ions (e.g. silver thiosulfate), and 2,5-norbornadiene inhibit ethylene action.

Plant growth regulators have also been used to protect crops from the effects of environmental stress. Gianfagna, T. J. et al. "Mode of Action and Use of Growth Retardants in Reducing the Effects of Environmental Stress on Horticultural Crops": Karssen, C. N. et al. (eds.) *Progress in Plant Growth Regulation*, pp. 778–87 (1992). For example, researchers found that if ethephon was applied at a low rate (0.08 mM) it significantly delayed bloom in peach and reduced side effects. Researchers also found that ethephon increased the yields and hardiness of several horticultural plants.

Although PGRs have been developed as a means to improve agricultural crop yields, certain obstacles make the actual use of PGRs prohibitive. For example, many of the compounds display phytotoxicity. Other compounds are difficult to synthesize.

Many compounds require high rate applications to be effective. For example, PCT Application WO 93/07747, incorporated herein by reference, describes an improvement in a plant growth factor by applying aminoethoxyvinylglycine ("AVG"), an inhibitor of ethylene biosynthesis, to cotton plants. As the rate of AVG treatment increased, so did the improvement. (WO 93/07747, Examples 2–4). Assuming that a spray volume of 500 l/ha was used, the rates of application described in WO 93/07747 would be approximately 62.5 to 500 grams active ingredient/hectare (g ia/ha). The maximum rate response occurs at the highest rates.

High rate applications may result in a significant waste of material and may result in the discharge of the PGRs into the surrounding environment. Also, although many of these compounds may induce a beneficial growth habit, they do not provide consistent improvement in plant growth factors. Other compounds may lose their effectiveness or cause a reduction in yield when applied to species which are under some form of environmental stress.

Thus, it is an object of the invention to formulate a PGR composition that improves a plant growth factor, such as yield, in cotton.

SUMMARY OF THE INVENTION

Provided herein is a method of improving at least one plant growth factor in a plant comprising administering to the plant an effective amount of a mixture of mepiquat chloride and aminoethoxyvinylglycine. The method is carried out preferably in cotton. Also provided herein is a composition comprising aminoethoxyvinylglycine and mepiquat chloride in an amount effective to increase the yield of cotton wherein such increase is greater than the combined total increase of plants treated with aminovinylglycine alone and mepiquat chloride alone as compared to untreated plants.

An improvement in a plant growth factor is defined as an agronomic improvement of plant growth such as increased floral (square) initiation, increased flower retention, increased fruit retention, increased square retention, increased boll retention, increased root growth, decreased internode length, increased stress tolerance, decreased wilting, decreased senescence, darker green pigmentation, increased germination rate, increased tolerance to low temperatures, and increased crop yield. That is, a favorable alteration of the physiology or growth of plants or an increase or decrease in plant growth which leads to an economic or agronomic benefit. Improvement in growth factors that result from the inhibition of ethylene production is preferred.

The methods and compositions as embodied by the combined treatment with AVG and mepiquat chloride provide surprising and unexpected results over both plants treated with AVG alone and over plants treated with mepiquat chloride alone.

DETAILED DESCRIPTION OF THE INVENTION

The method and composition of the present invention are best carried out at application rates wherein the AVG is applied at rates of greater than 12 g/ha. Preferably, the AVG is applied a rate greater than 12 g/ha, including the range from about 12 g/ha to about 101 g/ha. In another embodiment of the invention, the AVG is applied at a rate greater than about 31 g/ha, including the range of about 31 g/ha to about 100 g/ha, most preferably the AVG is applied at a rate greater than or equal to about 101 g/ha.

The mepiquat chloride is preferably applied at rates of from about 12 g/ha up to about 200, most preferably at about 12 g/ha.

An effective number of applications can be made throughout the growing season. Preferably, the application is performed from one to about ten times during the growing season, most preferably from one to about four times during the growing season. The AVG and mepiquat chloride may be applied in combination or as single applications by methods known in the art.

Other rates useful for carrying-out the invention may be developed using this specification and routine optimization.

The present invention finds its best results in cotton. Preferred formulations of the invention include those formulations that provide AVG in an effective amount to obtain consistent improvement in a plant growth factor, that is, those formulations that provide statistically significant improvement (e.g., where P=0.15 or less) when compared to untreated plants wherein the improvement is obtained more than about 50% of the time, preferably more than 60% of the time, more preferably more than 75% of the time and most preferably more than 90% of the time.

The formulations described in this invention are generally applied to the foliage prior to bud and flower development but they can also be applied to the foliage, buds, flowers, or bolls beginning at early bud development (e.g., matched square in cotton) in one to four sequential applications. If sequential applications are used, applications are preferably timed at approximately 10 to 14 days apart. When applied by spraying, the active ingredient is generally mixed with water as a carrier solution in a dilution sufficient to cover the area. Typically, the spray volume of the aqueous treatment solution would be about 150 to 500 l/ha for arable crops and up to about 1,500 l/ha for fruits tress. Soil drenching is another method of application that is useful when practicing the invention.

Accordingly, the present invention provides a method which improves the economic or agronomic output of agricultural crops and decreases the amount of material that needs to be used to obtain improvement in a plant growth factor.

The following example is illustrative only and is not meant to limit the invention in any manner.

EXPERIMENT 1

Technical grade AVG (85%) was provided by Abbott Laboratories. A 4.2% aqueous liquid formulation of PIX® (mepiquat chloride) was used in the trials. AVG was applied alone or in combination with 12 g ai/ha PIX® mepiquat chloride plant growth regulator at rates of 6, 12, 31, and 100 g ai/ha. Untreated plants were used as a control. Treatment timing began at match-head (size) square and continued every 10– 14 days thereafter for a total of four sequential applications. Plots were 6 rows wide by 40 ft. long and the treatments were replicated four times. In 3 trials, ten plants per plot were destructively sampled and mapped twice during the season. The first mapping was conducted approximately 10–14 days after the second treatment and the second mapping was conducted prior to harvest. In 2 trials, only the pre-harvest mapping was conducted. The center two rows of each plot were harvested, and seed cotton yields recorded. A total of 5 trials were conducted. One trial was moisture-stressed.

The combination of 100 g ai/ha AVG+mepiquat chloride significantly increased the yield by 30% in one trial, and by 11% (non-significant) in another. AVG showed an improvement in yield (1%) at a rate of 31 g ai/ha. A yield decrease was recorded in one trial where AVG was applied alone at 6 g ai/ha. No other significant yield differences were obtained in the remaining trials. Yield data are summarized in the attached table.

TABLE 1

AVG/Mepiquat Chloride Cotton Trials - Yield Data from 5 Trials

| | Relative Yield compared to mepiquat chloride (%) | | | | Relative Yield Compared to Untreated (%) | | | | PIX alone |
|---|---|---|---|---|---|---|---|---|---|
| Rate(g ai/ha) | 6 | 12 | 31 | 100 | 6 | 12 | 31 | 100 | |
| Location | | | | | | | | | |
| North Carolina | 1 | 4 | 1 | 11 | 4 | −4 | 1 | 3 | −4 |
| Louisiana | 12 | −6 | 7 | 30 | 2 | 11 | 5 | 4 | −15 |
| California | | | | | | | | | |
| (1) | −6 | −2 | 5 | 0 | −21 | −12 | −15 | −3 | −17 |
| (2) | −1 | −3 | −6 | −2 | −18 | −10 | −20 | −10 | −10 |
| Mississippi | −1 | 1 | 6 | 2 | −3 | −3 | −4 | −5 | 5 |
| Sum | 5 | −6 | 13 | 41 | −36 | −18 | −33 | −11 | −41 |
| Count | 5 | 5 | 5 | 5 | 5 | 5 | 5 | 5 | 5 |
| Mean Relative Yield (%) | 1 | −1 | 3 | 8 | −7 | −4 | −7 | −2 | −8 |
| Freq. Positives | 2 | 2 | 4 | 3 | 2 | 1 | 2 | 2 | 1 |
| % Freq. Pos. | 40% | 40% | 80% | 60% | 40% | 20% | 40% | 40% | 20% |

In this study, AVG and mepiquat chloride applied alone provided no yield benefit at all rates. No yield benefit was noted under moisture-stressed conditions. However, combinations of AVG and mepiquat chloride provided increased yield as the application rate of AVG was increased to 31 g ai/ha and greater. Alhough the combination composition, provided the greatest yield benefit (+8% over mepiquat chloride) when AVG was applied at a rate of 100 g ai/ha, the frequency of positive yield data was greater in the plants treated with the combination composition at a rate of 31 g ai/ha.

The first mapping data from the North Carolina site showed an increase in fruiting structures and retention in the plants treated with 100 g ai/ha AVG applied alone (not significant, p=0.05), but the same rate combined with mepiquat chloride tended to decrease the number of fruiting structures. Also, a decrease (p=0.05) in the number of fruiting branches at the North Carolina site was observed after treatment with the combination of AVG and mepiquat chloride (100 g ai/ha AVG). Lower rate combinations (6 and 12 g ai/ha AVG) tended to increase retention over plants treated with mepiquat alone,® alone. A decrease in plant height with the combination (100 g ai/ha AVG) was observed in one trial.

In the second mapping, a significant increase in open bolls was obtained with 31 gi/ha AVG applied alone in one trial. No significant effects from AVG alone or in combination with PIX® were noted in the second mappings of the remaining trials. Some increases were noted in retention of fruiting structures, but these were not consistent among the trials.

The invention has been described with reference to various specific embodiments. However, many variations and modifications may be made while remaining within the scope and spirit of the invention.

We claim:

1. A method of improving yield in a cotton plant comprising administering to the foliage of the plant a mixture of mepiquat chloride and aminoethoxyvinylglycine wherein the aminoethoxyvinylglycine is applied at a rate from about 12 g/ha to about 100 g/ha.

2. The method of claim 1 wherein the aminoethoxyvinylglycine is applied at a rate ranging from about 31 g/ha to about 100 g/ha.

3. The method of claim 1 wherein the aminoethoxyvinylglycine is applied at a rate of about 100 g/ha.

* * * * *